(12) United States Patent
Leboucher et al.

(10) Patent No.: US 6,204,329 B1
(45) Date of Patent: Mar. 20, 2001

(54) POLYSILOXANE-POLYBUTYLENE COPOLYMERS

(75) Inventors: Marie-Agnes Leboucher, Belgium (FR); Sian Rees, Pontypridd (GB); Anne-Marie Vincent, Belgium (FR)

(73) Assignees: Dow Corning S.A., Seneffe (BE); Dow Corning Ltd., Barry (GB)

( * ) Notice: Subject to any disclaimer, the term of this patent is extended or adjusted under 35 U.S.C. 154(b) by 0 days.

(21) Appl. No.: 09/345,220

(22) Filed: Jun. 30, 1999

(51) Int. Cl.[7] ............................................. C08F 10/10
(52) U.S. Cl. ............................... 525/106; 525/100; 528/15
(58) Field of Search ................... 525/100, 106; 528/15

(56) References Cited

U.S. PATENT DOCUMENTS

| | | | |
|---|---|---|---|
| 4,758,631 | 7/1988 | Kennedy et al. | 525/245 |
| 4,808,664 | 2/1989 | Saam | 525/106 |
| 4,904,732 | 2/1990 | Iwahara et al. | 525/100 |
| 5,061,762 * | 10/1991 | Fleischmann et al. | |
| 5,247,021 | 9/1993 | Fujisawa et al. | 525/254 |
| 5,516,870 | 5/1996 | Biggs et al. | 528/15 |
| 5,646,215 | 7/1997 | Lee | 525/285 |
| 5,663,245 | 9/1997 | Kennedy et al. | 525/479 |
| 5,741,859 | 4/1998 | Saxena et al. | 525/106 |
| 5,789,503 * | 8/1998 | Graiver et al. | |
| 6,084,030 * | 7/2000 | Janssen et al. | |

OTHER PUBLICATIONS

Macromolecules, "Synthesis, Characterization, and Properties of Stars Consisting of Many Polyisobutylene Arms Radiating from a Core of Condensed Cyclosiloxanes" vol. 30, pp. 3204–3214, 1997.

* cited by examiner

*Primary Examiner*—Robert Dawson
*Assistant Examiner*—Marc S. Zimmer
(74) *Attorney, Agent, or Firm*—James L. De Cesare

(57) ABSTRACT

A polysiloxane-polybutylene copolymer having polybutylene chains grafted onto a polysiloxane backbone which has a variety of properties which render it valuable for applications in personal care.

3 Claims, No Drawings

POLYSILOXANE-POLYBUTYLENE COPOLYMERS

FIELD OF THE INVENTION

The present invention relates to novel polysiloxane-polybutylene copolymers. Specifically, the present invention relates to such copolymers in which polybutylene chains are grafted onto polysiloxane backbones. These copolymers are particularly suited for uses in the personal care industry.

BACKGROUND OF THE INVENTION

The combination of silicon-containing molecules with polybutylene is known in the art, for instance, Iwahara et al. in U.S. Pat. No. 4,904,732 teach the formation of an isobutylene polymer having at least one silicon-containing group which is crosslinkable by the formation of a siloxane bond. The polymer described therein is said to be curable at room temperature to produce materials with weatherability, weather resistance, heat resistance, electric isolation and gas impermeability. This patent does not, however, describe polysiloxane-polybutylene copolymers in which polybutylene chains are grafted onto polysiloxane backbones.

Similarly, Saam in U.S. Pat. No. 4,808,664 teaches the formation of polyisobutylene oligomers containing siloxane functional terminal groups. This patent teaches that such materials cure at room temperature in the presence of moisture. Again, however, the patent teaches a main chain of isobutylene monomer units with a siloxane functional terminal unit as opposed to polysiloxane backbone copolymers with polybutylene chains grafted thereon as claimed herein.

Kennedy et al. in U.S. Pat. No. 5,663,245 teach novel multi-arm polymers comprising polyisobutylene arms connected to a well-defined siloxane core. This patent teaches that the resultant materials are acid stable, have low viscosity with high molecular weight, and are useful as motor oil additives. This patent, however, does not describe the copolymers claimed herein.

In U.S. Pat. No. 5,741,859, there is described a method of preparing a polyisobutylene-siloxane block copolymer via non-equilibrium anionic polymerisation of a diorganocyclotrisiloxane using a silanolate functional polyisobutylene as the initiator. Resulting copolymers are described and include certain di-block, tri-block, branched or star copolymers.

We have now discovered novel polysiloxane-polybutylene copolymers which have both siloxane and organic copolymer characteristics and, as such, are particularly useful in the personal care industry.

BRIEF SUMMARY OF THE INVENTION

The present invention provides in one of its aspects a polysiloxane-polybutylene copolymer having the polybutylene grafted onto a polysiloxane backbone, said copolymer having the structure $$R_aX_{(3-a)}Si-O-(R_2SiO)_q-(RXSiO)_y-SiX_{(3-a)}R_a$$

wherein each R is independently selected from the group consisting of hydrogen, hydroxyl, alkoxy, halogen, siloxane units, organic groups having from 1–30 carbon atoms and substituted organic groups having from 1–30 carbon atoms, X is a polybutylene having a molecular weight greater than about 500, a is 2 or 3, q is a positive integer with a value of at least 1 and y is a positive integer with a value of at least 2.

The resultant copolymers have both organic and silicone characteristics and, as such, have a variety of utilities. For instance, the copolymers may be used in cosmetic and medical utilities where it is desirable to have materials with both silicone and organic characteristics. Similarly, the copolymers are useful as compatibilizers for silicone and organic materials and are useful in polishes, coatings, lubricants, textiles and the like.

DETAILED DESCRIPTION OF THE INVENTION

The copolymers of the invention have the structure:

In this structure, each R is independently selected from the group consisting of hydrogen, hydroxyl, alkoxy, halogen, siloxane units, organic groups having from 1–30 carbon atoms and substituted organic groups having from 1–30 carbon atoms. The alkoxy groups can be, for example, methoxy, ethoxy, propoxy and the like. The halogens can be, for example, chlorine, bromine and the like. The siloxane units can be, for example, dimethylsiloxane units incorporated to form resinous polysiloxane structures. The organic groups can include, for example, alkyls such as methyl, ethyl, propyl, butyl, nonyl, dodecyl, tetradecyl, hexadecyl, octadecyl, eicosyl ($C_{20}$) and tricontyl ($C_{30}$), cycloalkyls such as cyclohexyl, unsaturated alkenyls or alkynyls such as vinyl, allyl and hexenyl, aryls such as phenyl, and the like. If desired the organic groups can be substituted with hetero atoms such a nitrogen, sulfur, halogens, silicon and oxygen. For example, the organic R groups can contain silicon and oxygen atoms (e.g., siloxane units), hydroxyl groups, alkoxy groups or nitrogen atoms. In one preferred embodiment of the invention, a majority of the R groups (e.g., 80%) comprise methyl groups. In another embodiment of the invention, at least one of the R groups comprise an organic group having form 10 to 30 carbon atoms to add additional organic characteristics.

It should be noted that the R groups can be different in the same unit. For instance, the ($R_2SiO$) unit could comprise (MeOctSiO), (MeDDSiO)or (MePhSiO) (Me=methyl, Oct= octyl, DD=dodecyl and Ph=phenyl). Similarly, there could be different ($R_2SiO$) units in the same copolymer. For instance, there could be (MeOctSiO), (MeDDSiO) and ($Me_2SiO$) units in the same polymer (Me=methyl, DD=dodecyl and Oct=octyl).

In the above structure I, X is a polybutylene. Such polybutylenes have repeating units of the structure

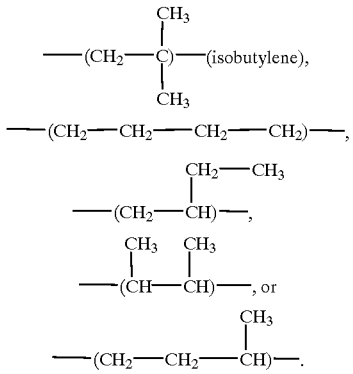

These polymers are typically terminated at one end with a hydrogen, an alkyl group, a halogen, or other conventional chain terminating groups and at the other end with an olefinic group as set forth below. Preferred are polymers with repeating isobutylene units (i.e., polyisobutylene).

The polybutylene chains which comprise X generally have a number average molecular weight of at least 500 and may go up to several hundred thousands, preferably in the range of 500 to about 50,000 and most preferably 1000 to about 20,000. In a preferred embodiment, the polybutylene unit is a poly-isobutylene with a number average molecular weight in the range of about 1000 to 20,000.

In the above structure I, a is 2 or 3, q is a positive integer, preferably 2 to 200, and y is a positive integer, with a value of from 2 preferably up to 200.

In one embodiment of the invention, the copolymer is of the structure:

$$R_3Si-O-(R_2SiO)_q-(RXSiO)_y-SiR_3 \qquad II$$

wherein R, X, q and y are as defined above.

In a preferred embodiment, a majority of the R groups are methyl and X is polyisobutylene. In another preferred embodiment, the ($R_2SiO$) units comprise ($CH_3RSiO$) units, wherein R is as defined above. In yet another preferred embodiment, the ($R_2SiO$) units comprise substantially (($CH_3$)$_2SiO$) units. In yet another preferred embodiment, the ($R_2SiO$) units comprise ($CH_3RSiO$) units and ($CH_3ZSiO$) units, wherein R is as defined above and Z denotes an organic group with 10 to 30 carbon atoms. In yet another preferred embodiment, the ($R_2SiO$) units comprise substantially ($CH_3ZSiO$) units,
wherein Z=an organic group with 10 to 30 carbon atoms.

In yet another embodiment of the invention, the copolymers have the structure $$R_2X\,Si-O-(R_2SiO)_q-(RXSiO)_y-SiXR_2 \qquad VI$$

wherein R, X, q and y are as defined above. In a preferred embodiment, a majority of the R groups are methyl and X is polyisobutylene. In another preferred embodiment, the ($R_2SiO$) units comprise ($CH_3RSiO$) units, wherein R is as defined above. In yet another preferred embodiment, the ($R_2SiO$) units comprise substantially (($CH_3$)$_2SiO$) units. In yet another preferred embodiment, the ($R_2SiO$) units comprise ($CH_3RSiO$) units and ($CH_3ZSiO$) units, wherein Z=an organic group with 10 to 30 carbon atoms. In yet another preferred embodiment, the ($R_2SiO$) units comprise substantially ($CH_3ZSiO$) units, wherein Z=an organic group with 10 to 30 carbon atoms.

The above copolymers are made by reacting a polysiloxane with a polyisobutylene. In this reaction, the polysiloxane generally has a reactive group that reacts with a reactive group on the polyisobutylene. This reaction can be facilitated with temperature, curing agents, catalysts, or other appropriate means.

In a preferred embodiment, the polysiloxane has an Si—H group which reacts with a polyisobutylene having olefin termination in the presence of a catalyst by the hydrosilylation reaction.

Olefin terminated polyisobutylenes are known in the art and are commercially available, for instance, under the trade name GLISSOPAL by BASF. Examples of olefin termination include:

—$CH_2$—$CH=CH_2$

—$CH_2$—$C(CH_3)=CH_2$

—$CH_2=CH_2$

—($CH_2$)$_r$—$CH=CH_2$ and

—($CH_2$)$_r$—$C(CH_3)=CH_2$ wherein r is an integer of 1–10. Other olefin terminations are also functional herein.

Methods for making olefin terminated polybutylenes are also known in the art. They include, for example, the method of Kennedy et al. as described in U.S. Pat. No. 4,758,631. In this process, the polymerization of isobutylene is initiated with $BCl_3$ and a mono or oligo-tertiary chloride inifer followed by the addition of hexane, allyltrimethylsilane and $TiCl_4$. Likewise, Fujisawa et al. in U.S. Pat. No. 5,247,021 teach the production of an allyl terminated polyisobutylene polymer by mixing a cationically polymerizable isobutylene containing monomer, an organic initiator/chain transfer agent, a lewis acid such as $TiCl_4$ and an end-capping agent such as allyltrimethylsilane. Likewise, Lee in U.S. Pat. No. 5,646,215 teaches the production of polybutylenes with unsaturated groups by reacting an anhydride functional polybutylene with an allyl functional compound having at least one hydroxyl containing groups in its molecule. The resultant polymers have structures such as:

PB—$CH_2$—$CH_2=CH_2$ and

PB—$CH_2$—$CH(CH_3)=CH_2$ wherein PB is the polybutylene polymer.

Polysiloxanes having Si—H groups are also known in the art and are commercially available. The structure of these polysiloxanes will vary depending on the final copolymer to be produced. Specifically, when producing the copolymers of the invention, one starts with polysiloxanes in which there are sufficient Si—H bonds present where the desired polyisobutylene are to be attached.

Examples of polysiloxane having Si—H groups include:

$Me_3$—Si—O—($Me_2$Si—O)$_q$—(MeHSi—O)$_y$—$SiMe_3$ $Me_3$—Si—O—(MeOctSi—O)$_q$—(MeHSi—O)$_y$—$SiMe_3$ $HMe_2$—Si—O—($Me_2$Si—O)$_q$—(MeHSi—O)$_y$—$SiMe_2H$ wherein Me=methyl, Oct=octyl, q is 1–200, preferably 3–100, and y is 2–200, preferably 3–100.

The polysiloxanes having SiH groups are produced by methods known in the art. Typically, such polysiloxanes are produced by cohydrolyzing hydridosilanes with other silanes (e.g., dimethyldichlorosilane, methyloctyldichlorosilane, etc.) to produced the desired copolymers. Alternatively a SiH polymer, prepared as above without use of the methyloctyl dichlorosilane, may be reacted with unsaturated alkenes, e.g. 1-octene. These reactions, as well as other methods for making polysiloxanes having SiH groups, are described, for example, in Chemistry and Technology of Silicones by Noll.

The polysiloxanes having Si—H groups are reacted with the olefin terminated polyisobutylene in the presence of a hydrosilylation catalyst. Such hydrosilylation catalysts are known in the art and can include, for example, platinum and rhodium containing materials. These catalysts may take any of the known forms such as platinum or rhodium deposited on carriers such as silica gel or powdered charcoal, or other appropriate compounds such as platinic chloride, salts of platinum and chloroplatinic acid either as the commonly obtainable hexahydrate or the anhydrous form. Platinum or rhodium complexes may also be used e.g. those prepared from chloroplatinic acid hexahydrate and divinyltetramethyldisiloxane.

The hydrosilylation reaction proceeds quickly following, for example, the following route:

PSX—Si($CH_3$)$_2$—H+PIB—$CH_2$—C($CH_3$)=$CH_2$→PSX—Si($CH_3$)$_2$—$CH_2$—CH($CH_3$)—$CH_2$—PIB wherein PSX is a polysiloxane and PIB is a polyisobutylene.

This process can be run in a solvent or solventless. Preferably, the reaction is run solventless to reduce the toxicity of residual solvent in the final product, especially for personal care uses. In addition, the solventless process avoids a stripping step in the manufacturing process.

If desired, olefin terminated alkanes (e.g., 1-dodecene) can be included in the above reaction to react with some of the Si—H groups. In this manner, polymers with both polybutylene and higher alkyl functionality (e.g. $C_{8-30}$ for example $C_{12}$) can be created.

The copolymers of the invention have a number of properties which render them particularly advantageous. For instance, the copolymers have a high refractive index, they provide gloss to substrates (e.g., hair, lipstick), they can compatibilize silicones and organic materials (e.g., in cosmetic compositions containing such materials), they inhibit water penetration on or from substrates (e.g., water loss from the skin or hair), they adhere well to substrates (e.g., long-lasting cosmetics), and their high refractive index may reduce whitening of antiperspirants and deodorants.

The copolymers of the invention are useful in the standard applications for silicone polymers. Thus, they are useful for personal care applications such as on hair, skin, mucous, teeth, etc. In these applications, the silicone is lubricious and will improve the properties, e.g. resistance to wash-off, protection against dehydration, increased skin protection, of skin creams, skin care lotions, moisturizers, facial treatments such as acne or wrinkle removers, personal and facial cleansers, bath oils, perfumes, fragrances, colognes, sachets, sunscreens, pre-shave and after shave lotions, shaving soaps and shaving lathers. They can likewise be used in hair shampoos, hair conditioners, hair sprays, mousses, permanents, depilatories, and cuticle coats to provide conditioning, shine benefits and supporting curl retention. In cosmetics, they function as a levelling and spreading agent, e.g. decreasing transfer, for pigment in make-ups, colour cosmetics, foundations, blushes, lipsticks, eye liners, mascaras, oil removers, colour cosmetic removers and powders. They are likewise useful as a delivery system for oil and water soluble substances such as vitamins, organic sunscreens, ceramides, pharmaceuticals and the like. When compounded into sticks, gels, lotions aerosols and roll-ons, the copolymers of this invention impart a dry silky-smooth payout. Additionally, the copolymers can be used to add gloss to the hair, skin or lipstick, they can be used to compatibilize silicones and organic ingredients in cosmetic compositions, they can be used to moisturize skin or hair, they can be used to make long-lasting cosmetics, and they can be used to reduce whitening of antiperspirants and deodorants.

For use in lipsticks for example, it is preferred that the copolymers have a viscosity of no more than 5000 mPa.s at 25° C., preferably with a relatively high organic content, e.g. 75% by weight or more. A number of higher alkyl ($C_{10-20}$) silicon-linked substituents are preferably present in addition to the polybutylene substituents. A particularly preferred higher alkyl group is $C_{12}$ and the ratio of $C_{12}$ units to polybutylene units is preferably from 60/40 to 80/20.

It is preferred that silicone polybutylene copolymers for use in hair care formulations, which are intended to give higher gloss to treated hair, have a viscosity below 9000 $mm^2$/s at 25° C. Preferably they have from 10 to 60 silicon atoms in the siloxane chain, and a mixture of silicon-bonded $C_{12}$ groups and polybutylene groups, preferably in a number ratio of from 60/40 to 80/20. For curl retention, it is preferred to have a viscosity of at least 3000 $mm^2$/s, with a low level of higher alkyl groups linked to silicon, and a relatively high level of silicon-bonded polybutylene substituents. These materials also protect hair against dehydration, e.g. when subjected to hair dryers.

For use in skin care applications, in order to give skin protection, it is preferred that higher molecular weight polymers are used, as they give a better film formation, that some higher alkyl (e.g. $C_8$ to $C_{16}$) silicon-based substituents are present, with 5 to 30% of the silicon atoms having polybutylene substituents.

When used in personal care products, they are generally incorporated in amounts of about 0.01 to about 50 weight percent, preferably 0.1 to 25 weight percent, of the personal care product. They may be added to conventional ingredients for the personal care product chosen. Thus, they may be mixed with deposition polymers, surfactants, detergents, antibacterial ingredients, anti-dandruff agents, foam boosters, proteins, moisturising agents, suspending agents, opacifiers, perfumes, colouring agents, plant extracts, polymers, and other conventional care ingredients.

Beyond personal care, the copolymers of the invention are useful for numerous other applications such as textile fibre treatment, leather lubrication, fabric softening, release agents, lubrication, compatibilising organic and silicone materials, as polishes on, for example, wood, metal, plastic, leather, etc. and in many other areas where silicones are conventionally used.

The following Examples are provided so that one skilled in the art will more readily understand the invention. Unless otherwise indicated, all parts and percents are by weight and all viscosities are at 25° C. 'Me' represents a methyl group and PIB represents polyisobutylene. GLISSOPAL 1000 is an olefin terminated (—$CH_2$—$C(CH_3)$=$CH_2$) polyisobutylene polymer with Mn=1100 obtained from BASF. The platinum catalyst is chloroplatinic acid in isopropyl alcohol used in an amount to deliver about 15 ppm Platinum. The 1-dodecene was ALPHA-OLEFIN $C_{12}$ obtained from CHEVRON.

EXAMPLES

The following polysiloxanes having Si—H groups were used in the process described below:

Polysiloxane 1.

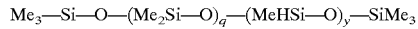

wherein on average q=3.5 and y=6.5.

Polysiloxane 2.

wherein y=60.

Polysiloxane 3.

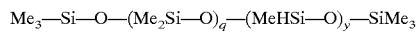

wherein q=18 and y=42.

Polysiloxane 4.

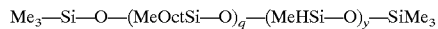

wherein y=42, q=18 and Oct=octyl.

Example 1

A copolymer was prepared by placing 5.2 g GLISSOPAL 1000 and the platinum catalyst in a vessel and then adding 94.8 g polysiloxane 1 dropwise at 65° C. under nitrogen atmosphere while stirring. The reaction mixture was then stirred under nitrogen atmosphere at 110° C. for several hours.

The resultant Si—PIB polymer (SP1) had a viscosity of 40 000 mm$^2$/sec and had the following structure:

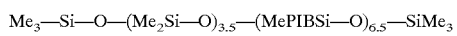

Me$_3$—Si—O—(Me$_2$Si—O)$_{3.5}$—(MePIBSi—O)$_{6.5}$—SiMe$_3$

Example 2

A copolymer was prepared in the same manner as Example 1 by reacting 45.9 g Glissopal 1000, platinum catalyst, 29.8 g 1-dodecene and 24.3 g polysiloxane 1.

The resultant Si—PIB polymer (SP2) had a viscosity of 650 mm$^2$/sec and the following structure (wherein DD=dodecyl):

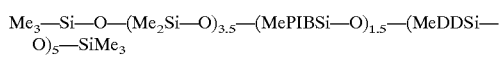

Me$_3$—Si—O—(Me$_2$Si—O)$_{3.5}$—(MePIBSi—O)$_{1.5}$—(MeDDSi—O)$_5$—SiMe$_3$

Example 3

A copolymer was prepared in the same manner as Example 1 by reacting 52.3 g Glissopal 1000, platinum catalyst, 33.9 g 1-dodecene, and 13.7 g polysiloxane 2.

The resultant Si—PIB polymer (SP3) had a viscosity of 20,000 mm$^2$/sec and had the following structure (wherein DD=dodecyl):

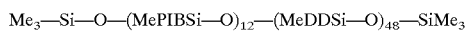

Me$_3$—Si—O—(MePIBSi—O)$_{12}$—(MeDDSi—O)$_{48}$—SiMe$_3$

Example 4

A copolymer was prepared in the same manner as Example 1 by reacting 89.7 g Glissopal 1000, platinum catalyst, and 10.7 g polysiloxane 3.

The resultant Si—PIB polymer (SP4) had a viscosity of 35,000 mm$^2$/sec and had the following structure:

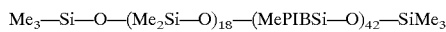

Me$_3$—Si—O—(Me$_2$Si—O)$_{18}$—(MePIBSi—O)$_{42}$—SiMe$_3$

Example 5

A copolymer was prepared in the same manner as Example 1 by reacting 54.3 g Glissopal 1000, platinum catalyst, 17.6 g 1-dodecene and 28.1 g polysiloxane 3.

The resultant Si—PIB polymer (SP5) had a viscosity of 1000 mm$^2$/sec and had the following structure (wherein DD=dodecyl):

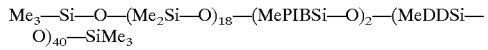

Me$_3$—Si—O—(Me$_2$Si—O)$_{18}$—(MePIBSi—O)$_2$—(MeDDSi—O)$_{40}$—SiMe$_3$

Example 6

A copolymer was prepared in the same manner as Example 1 by reacting 28.6 g Glissopal 1000, platinum catalyst, 39.9 g 1-dodecene and 31.5 g polysiloxane 4.

The resultant Si—PIB polymer (SP6) had a viscosity of 2000 mm$^2$/sec and had the following structure (wherein DD=dodecyl and Oct=octyl):

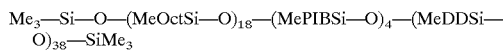

Me$_3$—Si—O—(MeOctSi—O)$_{18}$—(MePIBSi—O)$_4$—(MeDDSi—O)$_{38}$—SiMe$_3$

Examples 7–10

Additional copolymers were made by the process described in Example 1, using appropriate amounts of ingredients to give copolymers of the following structures:

Example 7: (polymer SP7)

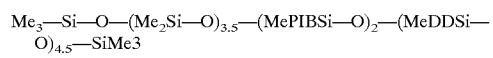

Me$_3$—Si—O—(Me$_2$Si—O)$_{3.5}$—(MePIBSi—O)$_2$—(MeDDSi—O)$_{4.5}$—SiMe3

Example 8: (polymer SP8)

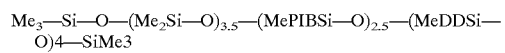

Me$_3$—Si—O—(Me$_2$Si—O)$_{3.5}$—(MePIBSi—O)$_{2.5}$—(MeDDSi—O)4—SiMe3

Example 9: (polymer SP9)

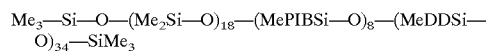

Me$_3$—Si—O—(Me$_2$Si—O)$_{18}$—(MePIBSi—O)$_8$—(MeDDSi—O)$_{34}$—SiMe$_3$

Example 10: (polymer SP10)

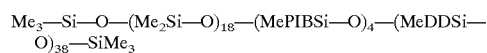

Me$_3$—Si—O—(Me$_2$Si—O)$_{18}$—(MePIBSi—O)$_4$—(MeDDSi—O)$_{38}$—SiMe$_3$

Application Examples

Example A

Sensory tests by 12 panelists were conducted to judge gloss and non-transfer (tested onto a glass surface) of formulated lipsticks with and without polymer SP7. Three formulations have been compared containing respectively 4% petrolatum as reference, 4% and 8% of SP7 polymer.

The means of the score for gloss given by each panelist for each formulation on a 1–10 scale (highest score means glossiest) was 4.8, 5.5 and 6 respectively for the reference, the 4% and the 8% copolymer. The non-transfer test showed that the reference was perceived to give 1.5 times as much transfer as the 4% lipstick, and 2 times as much as the 8% lipstick. Of course the lower values are better.

Example B

Sensory tests by 10 panelists have been conducted to judge shine on hair by combing swatches with compositions having polymers SP3, SP7 or SP9 and a control without Silicone-Organic copolymers. In each case the example polymers gave better shine than the control.

Example C

FTIR test were carried out on polymer SP8 after it had been applied to the skin of the arm of 3 panelists. The quantity of silicone is measured and the value is taken as 100%. After 15 min, the material was washed off, using three successive washes under normal washing conditions and the level of silicone is measured after each wash-off. This was compared with a standard silicone copolymer similar to SP8, but where no polyisobutylene substituents were present as the control. The amount of control left after the respective wash-off actions was 45, 30 and 20% of the original amount. For SP8, this was 80%, 60% and 55% respectively.

Example D

Visual tests were conducted with 4 times 3 panelists (repeated twice) of skin protection by applying skin care formulations using SP3 and SP6, in comparison with controls having no silicone polymers, Isopar® and Panalane®. After application, a colorant is applied to the skin, and the amount of colour left is evaluated. The lower the amount of colour, the better the skin protection given by the skin care formulation. The skin protection is indicated in the table below on a range of 0 to 7 (7 being best protection).

TABLE

| No Si | Isopar | Panalene | SP3 | SP6 |
|-------|--------|----------|-----|-----|
| 2     | 2.5    | 4        | 5   | 5.5 |

What is claimed is:

1. A polysiloxane-polybutylene copolymer comprising polybutylene grafted onto a polysiloxane backbone, the copolymer having the formula $$R_aX_{(3-a)}Si-O-(R_2SiO)_q-(RXSiO)_y-SiX_{(3-a)}R_a$$

wherein each R is independently selected from the group consisting of hydrogen, hydroxyl, alkoxy, halogen, siloxane units, organic groups having from 1–30 carbon atoms and substituted organic groups having from 1–30 carbon atoms, X is a polybutylene having a molecular weight greater than about 500, a is 2 or 3, q is a positive integer with a value of at least 1 and y is a positive integer with a value of at least 2, and wherein the $(R_2SiO)$ units comprise $(CH_3RSiO)$ units and $(CH_3ZSiO)$ units where Z is an organic group with 10 to 30 carbon atoms.

2. A polysiloxane-polybutylene copolymer comprising polybutylene grafted onto a polysiloxane backbone, the copolymer having the formula $$R_aX_{(3-a)}Si-O-(R_2SiO)_q-(RXSiO)_y-SiX_{(3-a)}R_a$$

wherein each R is independently selected from the group consisting of hydrogen, hydroxyl, alkoxy, halogen, siloxane units, organic groups having from 1–30 carbon atoms and substituted organic groups having from 1–30 carbon atoms, X is a polybutylene having a molecular weight greater than about 500, a is 2 or 3, q is a positive integer with a value of at least 1 and y is a positive integer with a value of at least 2, and wherein the $(R_2SiO)$ units comprise $(CH_3ZSiO)$ units where Z is an organic group with 10 to 30 carbon atoms.

3. A polysiloxane-polybutylene copolymer comprising polybutylene grafted onto a polysiloxane backbone, the copolymer having the formula $$R_aX_{(3-a)}Si-O-(R_2SiO)_q-(RXSiO)_y-SiX_{(3-a)}R_a$$

wherein each R is independently selected from the group consisting of hydrogen, hydroxyl, alkoxy, halogen, siloxane units, organic groups having from 1–30 carbon atoms and substituted organic groups having from 1–30 carbon atoms, X is a polybutylene having a molecular weight greater than about 500, a is 2 or 3, q is a positive integer with a value of at least 1 and y is a positive integer with a value of at least 2, and wherein at least one of the R groups comprise siloxane units for forming resinous polysiloxanes.

* * * * *